United States Patent [19]
Sato et al.

[11] Patent Number: 5,965,600
[45] Date of Patent: Oct. 12, 1999

[54] 3-(BIS-SUBSTITUTED PHENYLMETHYLENE) OXINDOLE DERIVATIVES

[75] Inventors: Atsushi Sato, Hasnno; Tetsuji Asao, Tokorozawa; Yuichi Hagiwara, Iruma; Makoto Kitade, Hanno; Yasundo Yamazaki, Iruma, all of Japan

[73] Assignee: Taiho Pharmaceutical Co., Ltd., Tokyo, Japan

[21] Appl. No.: 08/913,239

[22] PCT Filed: Jan. 16, 1997

[86] PCT No.: PCT/JP97/00066

§ 371 Date: Sep. 10, 1997

§ 102(e) Date: Sep. 10, 1997

[87] PCT Pub. No.: WO97/26242

PCT Pub. Date: Jul. 24, 1997

[30] Foreign Application Priority Data

Jan. 17, 1996 [JP] Japan ................... 8-005693
Feb. 2, 1996 [JP] Japan ................... 8-017636

[51] Int. Cl.⁶ .................................. A01N 43/38
[52] U.S. Cl. ............................ 514/419; 548/486
[58] Field of Search ................ 514/419; 548/486

[56] References Cited

U.S. PATENT DOCUMENTS 3,413,299 11/1968 Anthony .................... 260/295
3,428,649  2/1969 Plostnicks ................. 260/325

FOREIGN PATENT DOCUMENTS 60-222415 11/1985 Japan ............... A61K 31/09
1101794   1/1968 United Kingdom ....... C07D 99/04

OTHER PUBLICATIONS

Chemical abstract, vol. 60:4086a(Ber., 96(1963), 3328–37), 1996.

*Primary Examiner*—Dwayne C. Jones
*Attorney, Agent, or Firm*—Sughrue, Mion, Zinn, Macpeak & Seas, PLLC

[57] ABSTRACT

The present invention is directed to an oxindole derivative represented by formula (1):

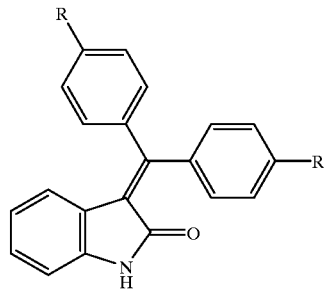

(1)

(wherein R represents a methyl group or a methoxy group), and pharmaceuticals containing the compound. The compound exhibits excellent granulation inhibiting activity while providing minimal liver toxicity and is useful as a pharmaceutical in the prevention and treatment of articular rheumatism, arteriosclerosis, hepatocirrhosis, etc., and also in the prevention and treatment of arthrosis deformans, psoriasis, gout, nephritis, angiitis, inflammatory intestinal diseases (ulcerative colitis, Crohn's disease), bronchitis, and chronic granulomatosis, etc.

6 Claims, 2 Drawing Sheets

3-(BIS-SUBSTITUTED PHENYLMETHYLENE) OXINDOLE DERIVATIVES

TECHNICAL FIELD

The present invention relates to a novel 3-(bis-substituted phenylmethylene)oxindole derivative and pharmaceuticals containing this compound.

BACKGROUND ART

Fibrosis of cells that brings about functional disorders of various organs and tissue is a great clinical problem in the alleviation of inflammation and the curing of wounds in organs or tissue. In joints, fibrosis of cells causes articular rheumatism, and in the liver, progress of cellular fibrosis leads to hepatic cirrhosis, causing jaundice and hypoproteinemia and eventually leading to liver failure. In blood vessels, fibrosis of vascular walls causes loss of elasticity of the walls, leading to arteriosclerosis. The first step of fibrosis is granulation, and therefore, it is considered that articular rheumatism,-hepatic cirrhosis, arteriosclerosis, etc. would be successfully treated if granulation could be inhibited.

In the development of pharmaceuticals, compounds having liver toxicity are problematic for successful development. In Nature No. 283, 397–398 (1980), it is reported that increased production of peroxisome, which causes hepatomegaly, is a carcinogenetic factor.

Therefore, there is strong demand for pharmaceuticals which exhibit excellent granulation inhibiting activity with minimal liver toxicity and which are thus advantageously used in clinical situations.

Analogs of a 3-(bis-substituted phenylmethylene)-oxindole derivative, which is the compound of the present invention, are disclosed in Ber., 96 (1963), 3328–37, Japanese Patent Publication (kokoku) No. 43-3195, and in U.S. Pat. No. 3,428,649. Of the analogs, 3-[bisphenylmethylene]-oxindole (compound a) of the following formula, disclosed in Ber., 96 (1963), 3328–37 is particularly close to the compounds of the present invention. However, that compound is merely disclosed as a synthesis intermediate, and no pharmacological activity is described at all.

(Compound a)

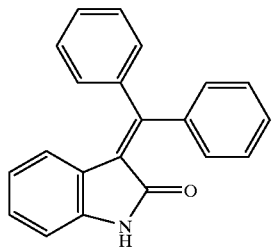

Japanese Patent Publication (kokoku) No. 43-3195 discloses, as a synthesis intermediate, an oxindole derivative represented by the following formula (2):

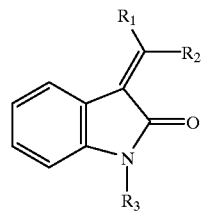

(wherein each of $R^1$ and $R^2$ represents lower alkyl, aryl, or pyridyl; and $R^3$ represents a hydrogen atom or lower alkyl).

However, the disclosure of 3-(bis-substituted phenylmethylene)oxindole derivative in that publication is in fact directed only to specific compounds in which $R^3$ is a methyl group and $R^1$ and $R^2$ are both unsubstituted phenyl groups, and to use as synthesis intermediates.

Accordingly, the object of the present invention is to provide a novel oxindole derivative which exhibits excellent granulation inhibiting activity while providing minimal liver toxicity and which is thus advantageously used as a pharmaceutical.

DISCLOSURE OF THE INVENTION

Under the above-described circumstances, the present inventors have conducted careful studies, and have found that the 3-(bis-substituted phenylmethylene)oxindole derivative represented by formula (1) exhibits excellent granulation inhibitory activity while providing minimal liver toxicity and can thus be advantageously used as a pharmaceutical, leading to completion of the invention.

Accordingly, the present invention provides an oxindole derivative represented by formula (1):

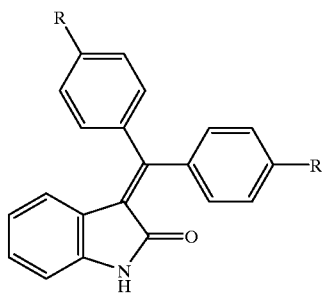

(wherein R represents a methyl group or a methoxy group).

The present invention also provides a pharmaceutical containing as the active ingredient the oxindole derivative (1)

The present invention also provides a granulation inhibitor containing as the active ingredient the oxindole derivative (1).

The present invention also provides a pharmaceutical composition containing the oxindole derivative (1) and a pharmacologically acceptable carrier.

The present invention also provides a granulation inhibitor composition containing the oxindole derivative (1) and a pharmacologically acceptable carrier.

The present invention further provides use, as a pharmaceutical, of the oxindole derivative (1).

The present invention still further provides use, as a granulation inhibitor, of the oxindole derivative (1).

The present invention additionally provides a preventive and therapeutic method for diseases caused by granulation, the method comprising administering to a patient the oxindole derivative (1).

BEST MODES FOR CARRYING OUT THE INVENTION

Figure 1:
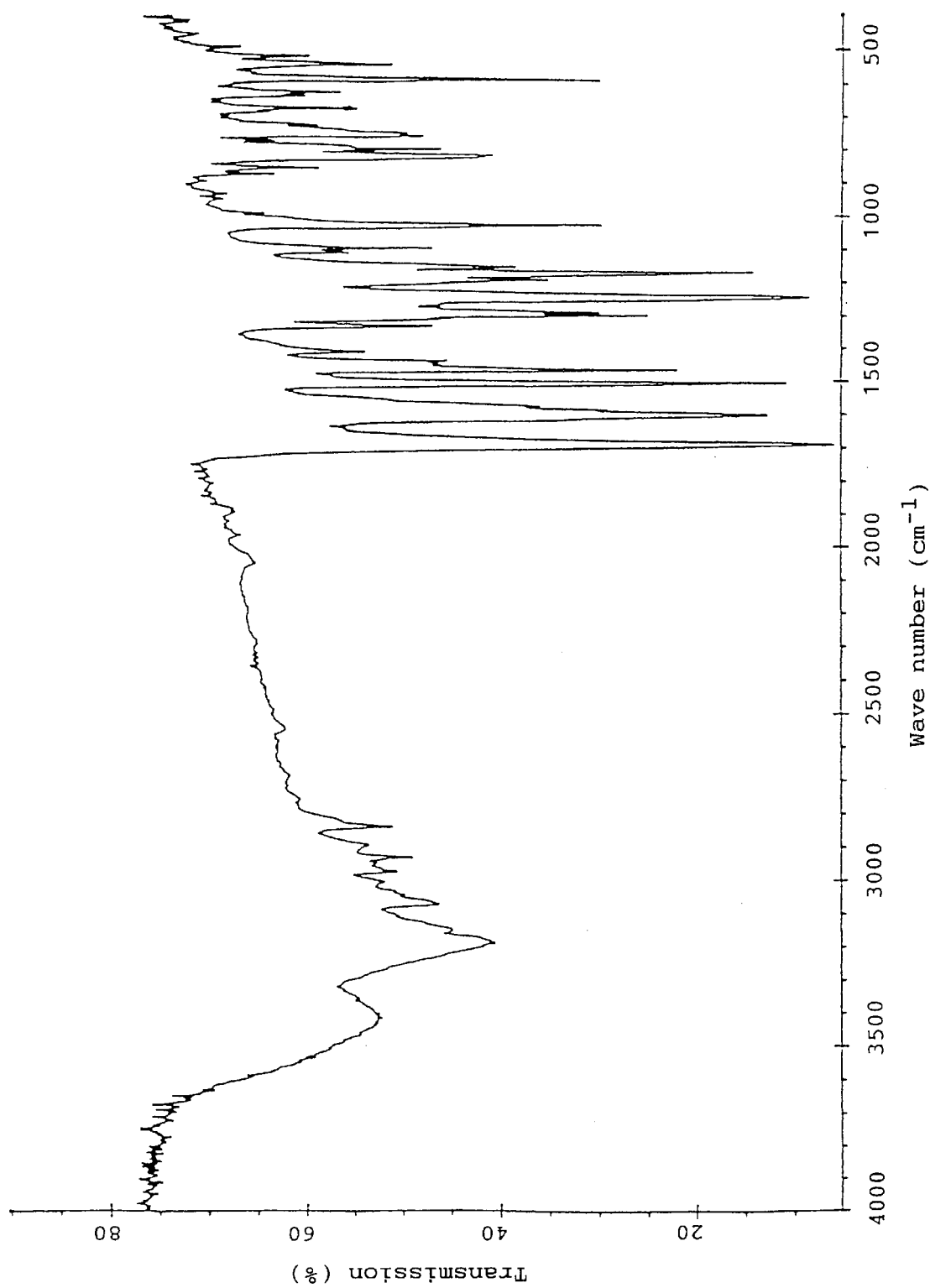
FIG. 1 is a representation of the IR spectrum of the oxindole derivative (Crystal 1) according to the present invention.

The oxindole derivatives of formula (1) of the present invention may be prepared in accordance with the following reaction scheme:

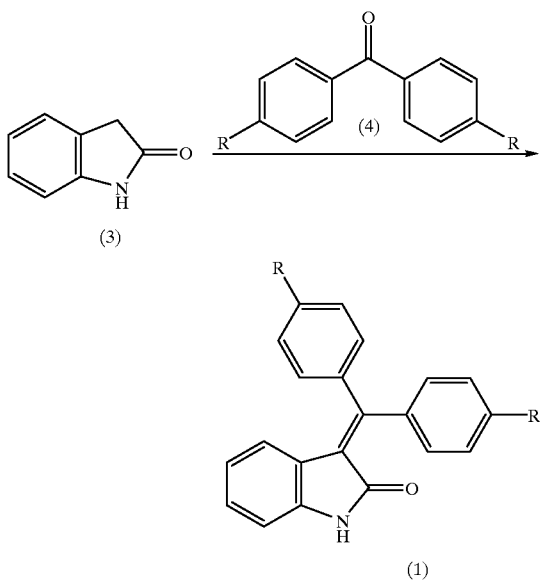

(wherein R has the same meaning as defined above).

The formula (1) compounds are obtained by reacting a known compound represented by formula (3) with another known compound represented by (4) in a suitable solvent in the presence of a base.

The solvent is not particularly limited so long as it does not affect the reaction, and examples thereof include toluene, tetrahydrofuran, dimethylformamide, dimethylsulfoxide, and dioxane. Examples of the base include inorganic bases such as sodium hydride, sodium hydroxide, potassium hydroxide, sodium hydrogencarbonate, potassium carbonate, and sodium carbonate; organic bases such as piperazine, piperidine, pyrrolidine, and pyridine. The reaction is preferably carried out using 1–3 moles of the formula (4) compound and 1–10 moles of a base with respect to 1 mole of the formula (3) compound. The reaction temperature is preferably between room temperature and 200° C., and the reaction time is preferably 1–24 hours.

The compounds represented by formula (3) may be prepared in accordance with the methods described, for example, in Journal of Medicinal Chemistry, 37, 2033 (1994), Tetrahedron Letters, 2587 (1979), Journal of American Chemical Society, 5508 (1974), Journal of American Chemical Society, 5512 (1974), or Tetrahedron, 24, 6093 (1968). The compounds represented by formula (4) may be prepared in accordance with the methods described, for example, in Organic Synthesis Collections, vol. I, p95 or Journal of Chemical Society, 529 (1951).

The formula (1) compound obtained in accordance with the above reaction scheme may be easily separated as crystals or oily matter by routine separation/purification means such as recrystallization, distillation, column chromatography, etc.

The formula (1) compound of the present invention encompasses solvates typified by hydrates, as well as polymorphic crystals.

The compounds of the present invention represented by the above-described formula (1) exhibit excellent granulation inhibitory activity, and thus are useful as pharmaceuticals for granulation-related diseases. Accordingly, it is possible to provide pharmaceutical compositions characterized by containing an effective amount of the compound of the present invention and a pharmacologically acceptable carrier.

When the compounds of the present invention are used as pharmaceuticals, they may be formed into drug preparations by routine methods through use of suitable pharmaceutical carriers. There may be incorporated a variety of carriers—such as vehicles, binders, disintegrators, lubricants, colorants, flavoring agents, odor improvers, and surfactants—that are widely used in common drugs.

When the pharmaceuticals of the present invention are used for the treatment of mammals including humans, the form of administration unit of the drugs is not particularly limited, and is suitably selected in accordance with the therapeutic purposes. Specifically, mention may be given of parenteral forms such as injections, suppositories, topical agents (ointments, patches, etc.), and aerosols; and peroral forms such as tablets, coated tablets, powders, granules, capsules, liquids, pills, suspensions, and emulsions.

The above-described various drugs are prepared by drug preparation methods well known in the art.

When solid preparations for peroral use—such as tablets, powders, and granules—are prepared, there may be used vehicles such as lactose, sucrose, sodium chloride, glucose, urea, starch, calcium carbonate, kaolin, crystalline cellulose, silicic acid, methylcellulose, glycerol, sodium alginate, and gum arabic; binders such as simple syrup, glucose solution, starch solution, gelatin solution, polyvinyl alcohol, polyvinyl ether, polyvinylpyrrolidone, carboxymethylcellulose, shellac, methylcellulose, ethylcellulose, hydroxypropylcellulose, water, ethanol, and potassium phosphate; disintegrators such as dry starch, sodium alginate, agar powder, laminaran powder, sodium hydrogencarbonate, calcium carbonate, polyoxyethylene sorbitan aliphatic esters, sodium lauryl sulfate, stearic monoglyceride, starch, and lactose; anti-disintegrators such as sucrose, stearic acid, cacao butter, and hydrogenated oils; absorption improvers such as quaternary ammonium bases and sodium lauryl sulfate; humectants such as glycerol and starch; adsorbing agents such as starch, lactose, kaolin, bentonite, and colloidal silica; and lubricants such as purified talc, stearates, boric acid-powder, and polyethylene glycol. If desired, tablets may have customary coatings such as sugar coating, gelatin coating, enteric coating, film coating, double coating, and multiple coating.

When pills are formed, there may be used carriers including vehicles such as glucose, starch, cacao butter, hydrogenated vegetable oils, kaolin, and talc; binders such as gum arabic powder, tragacanth gum powder, gelatin, and ethanol; and disintegrants such as laminaran and agar.

Capsules are prepared through mixing the compound with the aforementioned various carriers, and then packing the mixture into hard gelatin capsules, soft capsules, etc.

When suppositories are prepared, carriers such as polyethylene glycol, cacao butter, lanolin, higher alcohols, esters of higher alcohols, gelatin, semisynthesized glycerides, or Witepsole (registered trademark, Dynamite-Nobel) are used in combination with suitable absorption promoters.

When injection preparations are prepared, there may be used various carriers including diluents such as water, ethyl alcohol, macrogol, propylene glycol, ethoxylated isostearyl alcohol, polyoxyisostearic alcohol, and polyoxyethylene sorbitan aliphatic esters; pH regulators and buffers such as sodium citrate, sodium acetate, and sodium phosphate; and stabilizers such as sodium pyrosulfite, ethylenediaminetetraacetic acid, thioglycolic acid, and thiolactic acid. In this case, the pharmaceutical compositions may also contain NaCl, glucose, or glycerol in suitable amounts sufficient to prepare a isotonic solution. Moreover, ordinary solution adjuvants, soothing agents, and local analgesics may additionally be incorporated. Subcutaneous, intramuscular, and intravenous injection preparations are prepared by use of these carriers in customary methods.

Liquid preparations may be aqueous or oily suspension, solutions, syrups, or elixirs, which are prepared in accordance with customary methods using common additives.

When ointments, e.g., pastes, creams, or gels are prepared, commonly used bases, stabilizers, humectants, preservatives, etc. are incorporated as required, and then the ingredients are mixed to form drug preparations in accordance with customary methods. Examples of bases include white Vaseline, paraffin, glycerol, cellulose derivatives, polyethylene glycol, silicone, bentonite, etc. Examples of preservatives include methyl paraoxybenzoate, ethyl paraoxybenzoate, and propyl paraoxybenzoate.

When patches are prepared, the aforementioned ointments, creams, gels, pastes, etc. are applied onto conventionally-known supports through use of customary methods. Examples of suitable supports include woven or non-woven fabrics made of cotton, staple fiber, or chemical fiber; and films and foamed sheets made of soft vinyl chloride, polyethylene, polyurethane, etc.

The amount of the compound of the present invention to be incorporated into any of the above-described preparations varies in accordance with the form of preparation, administration route, and dosage regimen, and is suitably determined within a wide range. However, it is advisable that the compound be incorporated in an amount of 1–70% by weight based on the total weight of the preparation.

The route of administration, which is not particularly limited, is suitably determined in accordance with the form of preparation; age, sex, and other conditions of the patient; severity of the patient's symptoms, etc. For example, parenteral administration, peroral administration, rectal administration, administration in the oral cavity, and transdermal administration may be suitably used. Tablets, pills, liquids, suspensions, emulsions, granules, and capsules are orally administered; and suppositories are inserted into the rectum. Injection preparations may be intravenously administered in their own forms or in combination with commonly used adjuvants such as glucose and amino acids. If necessary, injection preparations are used singly for purposes of intraarterial, intramuscular, intracutaneous, subcutaneous, or intraperitoneal administrations. Ointments are applied onto the skin, mouth mucosa, etc.

The amount of the active ingredient of the present invention to be administered is suitably determined in accordance with the manner of administration; age, sex, and pathological conditions of the patient; identity of the compound of the present invention; and other factors. However, usually it is to be determined within the yardstick range of 0.1–300 mg/kg/day, preferably 0.5–100 mg/kg/day. The drug preparations of the present invention may be administered in a single administration or 2–4 divided administrations per day.

EXAMPLES

The present invention will be explained in more detail by the following examples, which should not be construed as limiting the present invention.

Example 1

Synthesis of 3-[bis(4-methoxyphenyl)methylene]-oxindole (Compound 1A):

(1) 10.0 g of oxindole was dissolved in 100 ml tetrahydrofuran, and 21.8 g of 4,4'-dimethoxybenzophenone was added thereto at room temperature. Subsequently, the temperature of the reaction was brought to 0° C. 9.0 g of 60% sodium hydride was added, and when generation of hydrogen ceased, the reaction mixture was refluxed with heat for 12 hours. After completion of reaction, the reaction mixture was cooled. Saturated aqueous ammonium chloride solution was added, followed by extraction with ethyl acetate. The extract was washed with water and saturated brine, dried over sodium sulfate, and then evaporated. The resultant crude product was recrystallized from methanol, to thereby obtain 22.8 g (yield 85%) of yellow crystals (Crystal 1). The physicochemical data are shown below. Also, the IR spectrum chart of the compound is shown in FIG. 1.

Melting point: 176–179° C.

Elementary analysis (%): C H N Calculated: 77.29 5.36 3.92 Found: 77.32 5.23 3.93

$^1$H-NMR (δppm) [Solvent: CDCl$_3$]: 3.84 (s, 3H), 3.88 (s, 3H), 6.51 (d, 1H), 6.65 (t, 1H), 6.70 (d, 1H), 6.87 (d, 2H), 6.93 (d, 2H), 7.04 (t, 1H), 7.25 (d, 2H), 7.31 (d, 2H), 8.40 (s, 1H)

Figure 2:
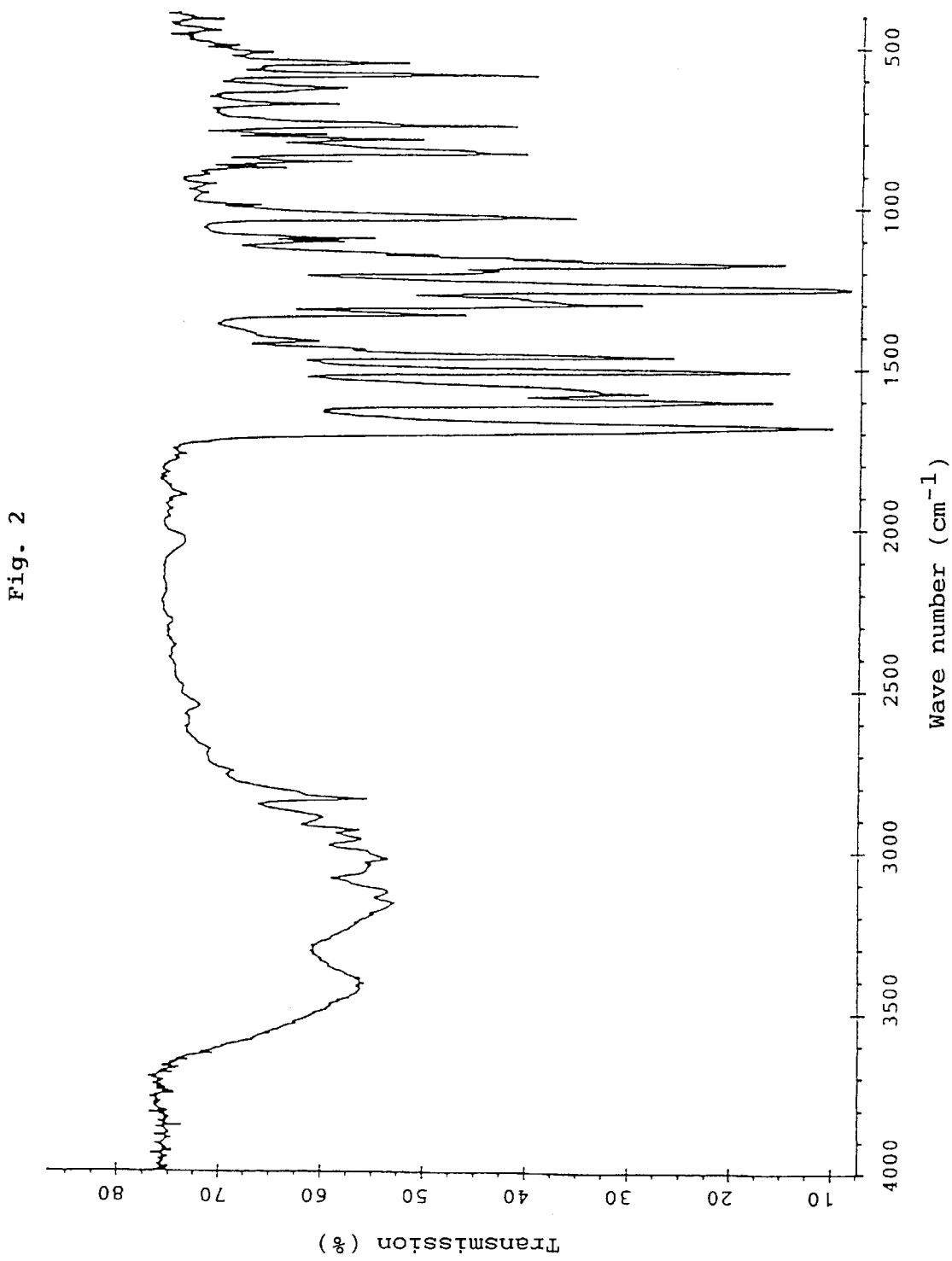
FIG. 2 is a representation of the IR spectrum of the oxindole derivative (Crystal 2) according to the present invention.

20 g of compound 1A (Crystal 1) obtained in (1) above was suspended in 200 ml n-undecane. The suspension was heated for 4 hours at approximately 160° C. and then cooled to 0° C., to thereby obtain 19.6 g (yield 98%) of orange-colored polymorphic crystals (Crystal 2) of Compound 1A. FIG. 2 shows the IR spectrum chart of the compound. The melting point was 203.5–205.5° C.

Example 2

Synthesis of 3-[bis(4-tolyl)methylene]-oxindole (Compound 1B)

The method of Example 1 was repeated with the exception that 4,4'-dimethylbenzophenone was used in place of 4,4'-dimethoxybenzophenone, to thereby obtain the title compound. The physicochemical data are shown below.

Melting point: 240–241° C.

Elementary analysis (%): C H N Calculated: 84.89 5.89 4.30 Found: 85.00 5.75 4.24

$^1$H-NMR (δppm) [Solvent: CDCl$_3$]: 2.37 (s, 3H), 2.43 (s, 3H), 6.47 (d, 1H), 6.65 (t, 1H), 6.73 (d, 1H), 7.07 (t, 1H), 7.13–7.26 (m, 8H), 7.79 (s, 1H)

Reference Example 1

Synthesis of 3-[bis(4-chlorophenyl)methylene]-oxindole (Compound c)

The method of Example 1 was repeated with the exception that 4,4'-dichlorobenzophenone was used in place of 4,4'-dimethoxybenzophenone, to thereby obtain the title compound. The physicochemical data are shown below.

Melting point: 206–208° C.

Elementary analysis (%): C H N Calculated: 68.87 3.58 3.82 Found: 69.09 3.29 3.79

$^1$H-NMR (δppm) [Solvent: CDCl$_3$]: 6.47 (d, 1H), 6.70 (t, 1H), 6.72 (d, 1H), 7.13 (t, 1H), 7.25 (d, 2H), 7.32 (d, 2H), 7.33 (d, 2H), 7.42 (d, 2H), 8.05 (s, 1H)

Test Example 1

Test of inhibiting granulation elicited by lipopolysaccharide (LPS)

The following test was performed in accordance with the method described in "Inflammation," vol. 11, No. 4, July 1991, 303–311. Briefly, a pouch was formed under the dorsal skin of each of 5-week-old male F344 rats under etherification, and on the following day, cerogen was injected. On the day later, lipopolysaccharide (LPS) was injected into the pouch in an amount of 5 ng/0.5 ml/pouch. Five days thereafter, the rats were dissected, and the weight of granule in the dorsal pouch of each rat was measured. The weights in the cases of treatment with test drugs and those in the cases of non-treatment were compared, and percentages of inhibition were obtained. The test drugs, i.e., Compound 1A (Crystal 1) and Compound 1B, were respectively suspended in 0.5% methylcellulose and administered to the rats each in an amount of 10 ml/100 mg body weight at a single time 2 hours before injection of LPS. The results are shown in Table 1. Independently, there were performed similar tests in which there were used, as comparative compounds, 3-(bisphenylmethylene)oxindole (Compound a) described in Ber., 96 (1963), 3328–37; (z)-3-[4-(acetyloxy)-5-ethyl-3-methoxy-1-naphthalenyl]-2-methyl-2-propenic acid (compound b: Japanese Patent Application Laid-Open (kokai) No. 2-256645) and 3-[bis(4-chlorophenyl)methylene]oxindole (Compound c) obtained in Reference Example 1. The results are shown in Table 1.

(Compound a)

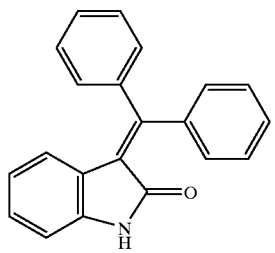

(Compound b)

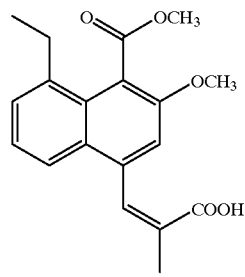

(Compound c)

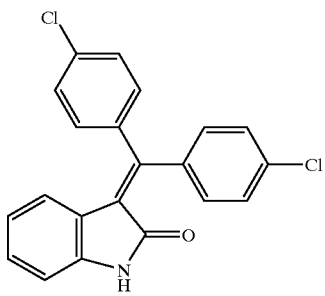

TABLE 1

| Compound | Dose (mg/kg) | Inhibition (%) |
| --- | --- | --- |
| 1A | 30 | 30.6 |
| (Crystal 1) | 100 | 44.1 |
| 1B | 30 | 45.0 |
| a | 30 | 16.3 |
|  | 100 | 17.6 |
| b | 100 | 42.0 |
| c | 100 | 10.8 |

From the above results, the compounds of the present invention were found to have effect equal to or greater than that of Comparative compound b, and in particular, remarkable granulation inhibiting activity of about 2–4 times that of Compound a or c, which are analogs of the compounds of the present invention. Moreover, the compounds of the present invention were confirmed to have excellent granulation inhibitory activity, about 10–15 fold that of compounds of formula (1) in which R is ethyl or ethoxy.

Test Example 2

Liver toxicity test

Test drugs (Compound 1A (Crystal 1) and Compound 1B) suspended in 0.5% methylcellulose were respectively administered to 4-week-old male S.D. rats in amounts of 300 mg/kg/10 ml by oral route for 7 days. After the final administration, the rats were left under fasting. Subsequently, the body weight of each rat was measured, and the rat was exsanguinated to death. The liver was removed and weighed. The weight of liver per 100 g of body weight was calculated. The percentage hypertrophy was obtained from the ratio of the liver weight of the non-treatment group to that of the treated group. The results are shown in Table 2. Independently, there was performed a similar test in which there was used, as a comparative compound, 3-(bisphenylmethylene)-oxindole (Compound a) described in Ber., 96 (1963), 3328–37. The results are shown in Table 2.

TABLE 2

| Compound | Hypertrophy (%) |
| --- | --- |
| 1A | 4.5 |
| (Crystal 1) |  |
| 1B | 2.3 |
| a | 13.6 |

The above results show that significant hepatomegaly was observed in relation to Comparative Compound a, whereas, quite inhibited hepatomegaly—about ⅙–⅓ that in the case of Comparative Compound a—was observed in relation to Compounds 1A and 1B.

Formulation Example 1 Tablets:

| | |
|---|---|
| Compound 1A (Crystal 1) | 200 mg |
| Cornstarch | 50 mg |
| Microcrystalline cellulose | 50 mg |
| Hydroxypropylcellulose | 15 mg |
| Lactose | 47 mg |
| Talc | 2 mg |
| Magnesium stearate | 2 mg |
| Ethylcellulose | 30 mg |
| Stearic monoglyceride | 4 mg |

The above formulation was processed with a routine method, to thereby prepare tablets each weighing 400 mg.

Formulation Example 2 Granules:

| | |
|---|---|
| Compound 1A (Crystal 1) | 300 mg |
| Lactose | 540 mg |
| Cornstarch | 100 mg |
| Hydroxypropylcellulose | 50 mg |
| Talc | 10 mg |

The above formulation was processed with a routine method, to thereby prepare packages of granules each package weighing 1,000 mg.

Formulation Example 3 Capsules:

| | |
|---|---|
| Compound 1B | 200 mg |
| Lactose | 30 mg |
| Cornstarch | 50 mg |
| Microcrystalline cellulose | 10 mg |
| Magnesium stearate | 3 mg |

The above formulation was processed with a routine method, to thereby prepare capsules each weighing 293 mg.

Formulation Example 4 Injection liquid:

| | |
|---|---|
| Compound 1B | 100 mg |
| Sodium chloride | 3.5 mg |
| Distilled water for injection | Suitable amount (2 ml per ampule) |

The above formulation was processed with a routine method, to thereby prepare an injection liquid.

Formulation Example 5 Syrup:

| | |
|---|---|
| Compound 1B | 200 mg |
| Purified sucrose | 60 g |
| Ethyl p-hydroxybenzoate sucrose | 5 mg |
| Propyl p-hydroxybenzoate sucrose | 5 mg |
| Perfume | Suitable amount |
| Colorant | Suitable amount |
| Purified water | Suitable amount |

The above formulation was processed with a routine method, to thereby prepare a syrup.

Formulation Example 6 Suppositories:

| | |
|---|---|
| Compound 1A (Crystal 1) | 300 mg |
| Witepsole W-35 | 1,400 mg |
| (Registered trademark of Dynamite-Nobel; Mixture of mono-, di-, and tri- glycerides of saturated fatty acid ranging from lauric acid to stearic acid) | |

The above formulation was processed with a routine method, to thereby prepare suppositories.

Industrial Applicability

The compound of the present invention exhibits excellent granulation inhibiting activity while providing minimal liver toxicity and is useful as a pharmaceutical in the prevention and treatment of articular rheumatism, arteriosclerosis, hepatocirrhosis, etc., and also in the prevention and treatment of arthrosis deformans, psoriasis, gout, nephritis, angiitis, inflammatory intestinal diseases (ulcerative colitis, Crohn's disease), bronchitis, and chronic granulomatosis, etc.

We claim:

1. An oxindole derivative represented by formula (1):

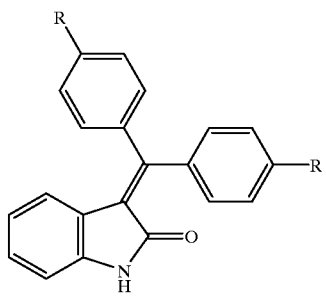

(1)

wherein R represents a methyl group or a methoxy group.

2. A pharmaceutical containing as the active ingredient the oxindole derivative as described in claim 1.

3. A granulation inhibitor containing as the active ingredient the oxindole derivative as described in claim 1.

4. A pharmaceutical composition containing the oxindole derivative as described in claim 1 and a pharmacologically acceptable carrier.

5. A granulation inhibitor composition containing the oxindole derivative as described in claim 1 and a pharmacologically acceptable carrier.

6. A preventive and therapeutic method for arteriosclerosis and articular rheumatism caused by granulation, comprising administering to a patient in need thereof an oxindole derivative represented by formula (1):

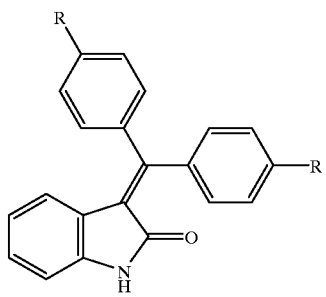

(1)

wherein R represents a methyl group or a methoxy group in an amount effective for inhibiting granulation.

* * * * *